United States Patent [19]
Kliegis

[11] Patent Number: 5,769,078
[45] Date of Patent: Jun. 23, 1998

[54] DEVICE AND PROCESS FOR PREPARING FOR AND SUPPORTING SURGICAL OPERATIONS

[76] Inventor: Ulrich Kliegis, Holtenauer Str. 273, D-24106 Kiel, Germany

[21] Appl. No.: 501,045
[22] PCT Filed: Feb. 15, 1994
[86] PCT No.: PCT/DE94/00156
 § 371 Date: Aug. 16, 1995
 § 102(e) Date: Aug. 16, 1995
[87] PCT Pub. No.: WO94/18899
 PCT Pub. Date: Sep. 1, 1994

[30] Foreign Application Priority Data

Feb. 16, 1993 [DE] Germany .......................... 43 04 570.7

[51] Int. Cl.$^6$ .................................................. A61B 17/00
[52] U.S. Cl. ....................... 128/653.1; 128/920; 623/901; 606/86
[58] Field of Search ................................ 128/653.1, 898, 128/920, 922; 606/130, 86, 87; 623/901; 395/924, 80, 94, 904

[56] References Cited

U.S. PATENT DOCUMENTS

| | | |
|---|---|---|
| 5,078,140 | 1/1992 | Kwoh . |
| 5,086,401 | 2/1992 | Glassman et al. .......................... 395/94 |
| 5,152,763 | 10/1992 | Johnson . |
| 5,185,809 | 2/1993 | Kennedy et al. . |
| 5,186,174 | 2/1993 | Schlöndorff et al. . |
| 5,299,288 | 3/1994 | Glassman et al. . |
| 5,360,446 | 11/1994 | Kennedy ................................... 623/16 |
| 5,365,996 | 11/1994 | Crook . |
| 5,370,692 | 12/1994 | Fink et al. . |
| 5,408,409 | 4/1995 | Glassman et al. . |
| 5,411,504 | 5/1995 | Vilas . |
| 5,539,649 | 7/1996 | Walsh et al. . |
| 5,554,190 | 9/1996 | Draenert . |
| 5,555,884 | 9/1996 | Nonomura .......................... 128/653.2 |
| 5,587,912 | 12/1996 | Andersson et al. . |

*Primary Examiner*—Marvin M. Lateef
*Assistant Examiner*—Shawna J. Shaw
*Attorney, Agent, or Firm*—Foley & Lardner

[57] ABSTRACT

A device and method for preparing for and supporting surgical operations includes a numerically controlled positioning appliance which is arranged in a predetermined or measurable geometric relationship with respect to an operating site. A surgical instrument, such as a machining tool or a holder for a graft, can be releasably connected to this positioning appliance for movement in relation to the operation site. A measurement appliance is used for measuring coordinates of the operation site in relation to a stationary reference system. The holder can be releasably secured to the positioning appliance or, alternatively, can be secured on a securing device which is stationary in relation to the reference system. The securing device is arranged in a predetermined or measurable geometric relationship with respect to the operation site. A data processing unit with memory controls the positioning appliance. The memory stores a data record of a three-dimensional structural image of the operation site. The three-dimensional image of the operation site is prepared from individual morphology data determined by noninvasive examination procedures prior to surgery. This image is used as the basis for the planning of osteotomy lines. The coordinates of the osteotomy lines are taken over in control commands for the positioning.

18 Claims, 1 Drawing Sheet

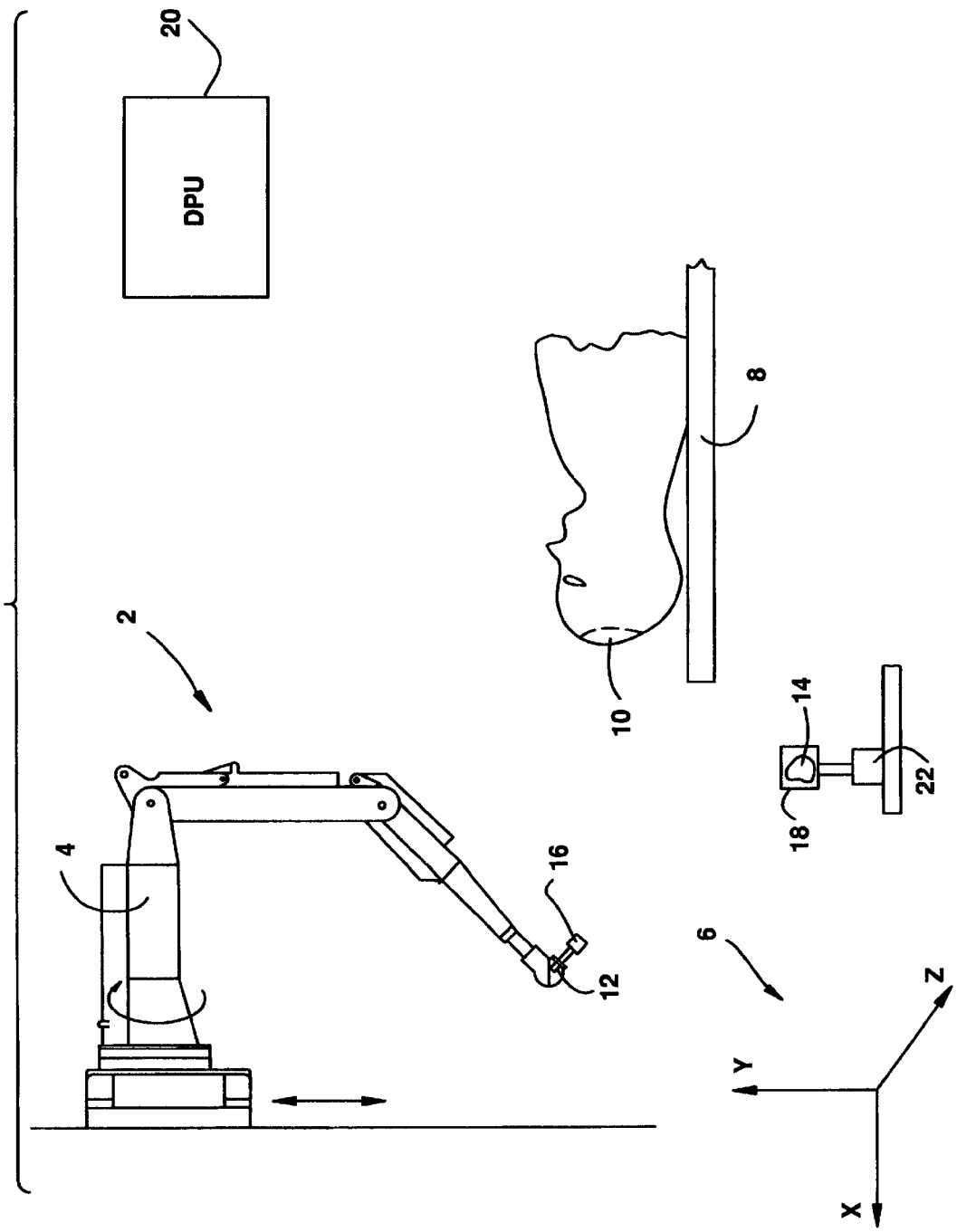

DEVICE AND PROCESS FOR PREPARING FOR AND SUPPORTING SURGICAL OPERATIONS

BACKGROUND

The invention relates to a device and a process for preparing for and supporting surgical operations, in particular for preparing for and supporting bone grafting operations and transposition osteotomies.

When grafting a bone fragment on the cranium, representing one example of bone grafting, a graft is taken, preferably from the area of the iliac crest, after the pathologically altered or inoperably destroyed bone fragment has been removed. The graft is then machined to remove material at its edges in order to match its external form as far as possible to the cranial opening so that it can be fitted into the cranial opening without any substantial edge joints, which delay the healing process.

In the past machining of the graft has been carried out by hand and requires great manual dexterity on the part of the surgeon and a good spatial imagination in order to produce, in a few machining steps, a graft which fits well. However, for less experienced or practiced surgeons, this procedure is very time-consuming on the one hand, since it necessitates frequently comparing the graft to the cranial opening in order to prevent too much material being removed. On the other hand, these surgeons in most cases choose a relatively simple geometric shape as the contour for the cranial opening and for the graft in order to make the matching of the graft easier. But the result of this is that more healthy bone tissue is often removed from the cranium than is necessary, and that accordingly a larger graft has to be removed too, which consequently slows down the healing process at the donor site for the graft.

SUMMARY OF THE INVENTION

The invention is based on the object of developing a process and a device which make it possible to match a graft, regardless of its shape, with great accuracy to a grafting site.

In the present device, this object is achieved according to the invention with the aid of a numerically controlled positioning appliance which is arranged in a predetermined or measurable geometric relationship with respect to an operation site and to which at least one surgical instrument, a machining tool for the machining of tissue or bone, or a holder for the graft, can be releasably. The invention is based on the idea of using the high precision of numerical controls in order to machine the graft when matching it and/or in order to position it subsequently at the grafting site until it has been fixed.

In the presents process, the solution according to the invention proposes determining the individual anatomical morphology in the area of an intended operation site prior to surgery, and preparing the determined data as the basis for planning and/or simulating the operation, and also for numerical control of at least one positioning appliance which is arranged in a predetermined or measurable geometric relationship with respect to the operation site and to which a surgical instrument, a machining tool for tissue or bone, or a holder for a graft, can be releasably connected.

In preferred embodiment of the invention a holder can be connected to the positioning appliance, on which holder the graft is releasably secured. The positioning appliance can in this case be used without removal of the holder, both for the computer-aided movement of the graft, at the time of its machining, with great accuracy in relation to a stationary machining tool, for example a milling head, and also for the positioning of the finished graft at the grafting site until it is secured to the site. Alternatively, the holder with the releasably secured graft can be designed such that it can be secured both with the positioning appliance and also stationary in a predetermined or measurable geometric relationship with respect to a reference system. While in the stationary state, the graft is machined into the intended shape by a machining tool connected to the positioning appliance, and then the graft can be positioned by the positioning appliance after exchanging the machining tool for the holder.

In order to ensure high positioning and machining accuracy both during the positioning and also during the shaping, a data processing unit is provided in accordance with a further preferred embodiment of the invention. The data processing unit has a memory in the data record is stored which reproduces in a three-dimensional system of coordinates the individual anatomical morphology of the grafting site which, in accordance with a further preferred embodiment of the invention, was determined prior to surgery by evaluating the results of noninvasive examinations, for example computed tomography, nuclear magnetic resonance tomography, ultrasound, X-ray or holographic examinations. Thus, for example, morphology data can be determined from a series of tomograms, arranged one after the other, of the operation site. In these examinations, the region of the body which is to be examined is advantageously recorded in layers by means of mutually parallel tomograms of sufficient resolution, and the data obtained are evaluated in the data processing unit in order to produce therefrom a three-dimensional structural image of the bones or organs in the area of the proposed operation site. The structural image can serve as a basis for the planning and simulation of the operation. Knowledge of the morphology of the tissue in the operation site facilitates the planning of the osteotomy lines and is also useful, after the osteotomy lines have been established, for searching for a suitable donor site for the graft, since the search with the aid of the data processing unit hugely increases the number of options which can be checked.

In accordance with another preferred embodiment of the invention, the positioning appliance is controlled by the stored data processing unit on the basis of the three-dimensional data record. The system of coordinates of the data record coincides with the reference system in which the movements of the positioning appliance take place, with respect to the origin of the coordinates, the number and orientation of the coordinate axes in relation to one another, and the scale. This can be effected with the aid of a mechanical, acoustic, or optical measurement device with which, before or during the operation, the coordinates of characteristic fixed points of the operation site are measured in relation to a reference point. The reference point is in a known geometric relationship to the origin of the coordinates of the manipulator arm. The same applies to the measurement of the exposed surfaces of the remaining healthy bone or tissue after the pathologically altered or damaged parts have been removed.

During the operation, this measurement device can also be used to measure the spatial form of the graft arranged on the stationary holder with respect to the reference system, before the graft is machined, and a machining tool connected to the positioning appliance can be guided, after correlation of the systems of coordinates by the data processing unit, along the previously measured surfaces of the remaining healthy bone which are in this case superposed synthetically on the graft.

In accordance with an advantageous embodiment of the invention, the positioning appliance has several degrees of freedom of movement, so that the surgical instrument connected to it, the machining tool, or the holder for the graft can adopt any desired spatial position.

In accordance with a further advantageous embodiment of the invention, the positioning appliance has at least one manipulator arm which, in the area of its free end, has a receiver. The surgical instrument, the machining tool or the graft holder can be inserted into the receiver.

A plurality of manipulator arms can be advantageously provided. It then is possible to connect to the receivers of the arms sensors for determining biological or physical parameters, such as muscle currents or brain currents or the pH in the area of the operation site. It is also possible to connect to the receivers surgical aids, for example hooks or the like, which hold the operation site open without fatigue and which can be displaced with high precision by controlling the manipulator arms.

DETAILED DESCRIPTION OF THE INVENTION

The invention is explained in greater detail hereinafter on the basis of an illustrative embodiment which is represented diagrammatically in FIG. 1. FIG. 1 shows a positioning appliance of a device according to the invention for supporting surgical operations.

The positioning appliance 2 represented in FIG. 1 consists chiefly of a numerically controlled manipulator arm 4 which can be moved with several degrees of freedom of movement in relation to a stationary reference system 6. A patient can be secured on a stationary operating support 8 in such a way that a proposed operation site 10 is located in the area of movement of a receiver 12 arranged at the free end of the manipulator arm 4. A surgical instrument, a machining tool 16 or a holder 18 for a graft 14 can be inserted into the receiver 12.

The movements of the manipulator arm 4, and thus the movements of the surgical instrument, the machining tool 16, or the holder 18 inserted into the receiver 12, are controlled by a data processing unit (DPU) 20 directly or indirectly by transmission of data to a numerical control system of the manipulator arm 4 itself.

The DPU 20 has a memory in which a 3D data record for a three-dimensional structural image of the operation site 10 is stored. The structural image comprises in its own system of coordinates the individual anatomical morphology of the grafting site which was determined prior to surgery by evaluating the results of noninvasive examinations, for example computed tomography, nuclear magnetic resonance tomography, ultrasound, X-ray, or holographic examinations. The individual anatomical morphology also was the basis for the planning of the osteotomy lines, which are likewise stored in the memory of the DPU 20.

An optical or mechanical measurement device (not shown) is used, after the patient has been secured on the operating support 8, to obtain the coordinates of characteristic points of the operation site 10, for example easily discernible bone features, in relation to the stationary reference system 6. The measurement data read into the DPU 20, is compared by the DPU 20 with the data record of the structural image. The system of coordinates of the structural image is brought into coincidence with the reference system 6 by computer means so that the structural image and the planned osteotomy lines can be superposed on the operation site 10. By this means, for example, after the osteotomy has been completed, the bone surfaces surrounding the graft 14 can be subjected to fine machining by the surgeon, with the aid of a machining tool 16 inserted into the receiver 12, for example a rotationally driven milling head, in order to cause the bone surfaces to coincide exactly with the stored osteotomy lines.

The measurement device is further used for measuring the graft 14 which is releasably secured on the holder 18. The holder 18, which has a shape similar to a small osteosynthesis plate, is for this purpose secured in a securing device 22 which is stationary in relation to the operating support 8 and which is likewise arranged in the area of movement of a machining tool 16 inserted into the receiver 12 of the manipulator arm 4. The coordinates of the boundary surfaces of the graft 14 are then determined, and the geometrical configuration of the previously measured surfaces of the remaining healthy tissue or bone is superposed on the graft 14 by computer means, along which surfaces the cutting or milling edge of the machining tool 16 inserted into the receiver 12 is then guided by the DPU 20 in order to match the boundary surfaces of the graft 14 as exactly as possible to the surfaces of the tissue or bone surrounding the graft 14. The movement of the manipulator arm 4 can nevertheless be controlled in such a way that a small joint of uniform thickness later remains in some places between graft 14 and the surrounding tissue or bone. The joint can be filled with bone cement in order to fix the graft 14 against displacement.

After the graft 14 has been shaped, the graft is then inserted together with the holder 18 into the receiver 12 and is positioned in correct alignment in the operation site 10 at the proposed grafting site. The movement of the manipulator arm 4 being controlled by the DPU 20.

The positioning appliance 2 can have additional numerically controlled manipulator arms, into whose receivers it is possible to insert, during the operation, sensors or surgical aids, such as hooks, in order, respectively, to transmit information on the particular status of biologically relevant parameters, for example the muscle currents or brain currents, from the operation site to a physiological monitoring system, and to hold the operation site open in a manner free from fatigue.

I claim:

1. A system for preparing for and supporting surgical operations, comprising:

a numerically controlled positioning appliance arranged in a measurable geometric relationship with respect to an operation site, said positioning appliance being movable in relation to the operation site;

a machining tool for machining tissue or bone and a holder for holding a graft, wherein one of said machining tool and said holder is adapted to be selectively releasably connected to said positioning appliance;

a securing device for releasably engaging said holder, said securing device being stationary with respect to a stationary reference system; and a data processing unit for controlling a position of said positioning appliance within said stationary reference system, said data processing unit having a memory;

wherein said memory of said data processing unit stores a data record of a three-dimensional structural image of the operation site, said data record containing the individual anatomical morphology of the grafting site, which is determined before surgery by evaluation of the results of noninvasive examinations, said data record being used to determine the dimensions of the graft and the dimensions of a diseased part of a bone to be cut out of the operation site, wherein said positioning appliance carries said machining tool to machine the graft according to the dimensions stored in said data record and, after removal of said machining tool, carries said holder to implant the graft at the operation site.

2. A system according to claim 1 wherein said measurable geometric relationship is predetermined.

3. A method for preparing for and supporting surgical operations, said method comprising the steps of:

performing a noninvasive examination of an area of an intended operation site before surgery;

evaluating the results of the noninvasive examination and determining an individual anatomical morphology;

storing data representing the individual anatomical morphology, the morphology data being usable as the basis for numerical control of a positioning appliance and as the basis for at least one of planning and simulating the operation;

resecting a graft according to the morphology data, the graft being substantially equal in size to an area of diseased tissue or bone to be resected from the operation site;

depositing the graft on a holder;

moving the holder and the graft via a positioning appliance to a securing device, the securing device being stationary with respect to a stationary reference system, the holder being releasably connected to the securing device;

resecting diseased tissue or bone from the operation site according to the morphology data; and moving the graft from said holder into the resected area at the operation site via the positioning appliance.

4. The system according to claim 1 further comprising:

a measurement appliance for measuring coordinates of the operation site in relation to said stationary reference system.

5. The system according to claim 1 wherein said securing device is arranged in a predetermined or measurable geometric relationship in relation to the operation site.

6. The system according to claim 1 wherein said memory of said data processing unit stores a data record for a three-dimensional image of planned osteotomy lines.

7. The system according claim 1 wherein said positioning appliance has several degrees of freedom of movement.

8. The system according to claim 1 wherein said positioning appliance has at least one manipulator arm.

9. The system according to claim 8 wherein said at least one manipulator arm has a free end and a receiver arranged proximate said free end.

10. The system according to claim 1 wherein said machining tool releasably connected to said positioning appliance is driven by a motor.

11. The system according to claim 10 wherein said machining tool comprises at least one of a cutting tool, a milling tool, and a drilling tool.

12. The system according to claim 1 wherein said holder for the graft comprises an osteosynthesis plate.

13. The method according to claim 3 wherein said step of determining an individual anatomical morphology is performed by at least one of computed tomography, nuclear magnetic resonance, X-ray, ultrasound, and holographic examinations.

14. The method according to claim 3 wherein said step of determining an individual anatomical morphology is performed by analyzing a series of tomograms, arranged one after the other, of the operation site.

15. The method according to claim 3 and further comprising the step of preparing a three-dimensional image of the operation site by analyzing the morphology data.

16. The method according to claim 15 wherein the three-dimensional image is used as a basis for the planning of osteotomy lines.

17. The method according to claim 15 wherein the positioning appliance is moved according to the coordinates of the osteotomy lines.

18. A method according to claim 3 and further comprising the step of shaping an outer surface of the graft via a machining tool to match a boundary of the resected area of diseased tissue or bone.

* * * * *